United States Patent
Righini et al.

(10) Patent No.: US 8,715,207 B2
(45) Date of Patent: May 6, 2014

(54) UNIVERSAL VALVE ANNULUS SIZING DEVICE

(75) Inventors: Giovanni Righini, Chivasso (IT); Felice G. Carlino, Borgomasino (IT); Giovanni Rolando, Chivasso (IT)

(73) Assignee: Sorin Group Italia S.r.l., Milan (IT)

(*) Notice: Subject to any disclaimer, the term of this patent is extended or adjusted under 35 U.S.C. 154(b) by 1076 days.

(21) Appl. No.: 12/727,098

(22) Filed: Mar. 18, 2010

(65) Prior Publication Data
US 2010/0249661 A1    Sep. 30, 2010

Related U.S. Application Data

(60) Provisional application No. 61/161,462, filed on Mar. 19, 2009.

(51) Int. Cl.
*A61B 5/103* (2006.01)

(52) U.S. Cl.
USPC ............. 600/587; 623/2.11; 606/198; 33/512

(58) Field of Classification Search
USPC ....... 600/587; 606/198, 90; 33/512; 623/2.11
See application file for complete search history.

(56) References Cited

U.S. PATENT DOCUMENTS

| | | |
|---|---|---|
| 3,363,442 A | 1/1968 | Kennedy et al. |
| 5,042,161 A | 8/1991 | Hodge |
| 5,360,014 A | 11/1994 | Sauter et al. |
| 5,489,296 A | 2/1996 | Love et al. |
| 5,522,884 A | 6/1996 | Wright |
| 5,560,487 A | 10/1996 | Starr |
| 5,669,919 A | 9/1997 | Sanders et al. |
| 5,672,169 A | 9/1997 | Verbeek |
| 5,693,066 A | 12/1997 | Rupp et al. |
| 5,698,307 A | 12/1997 | Levy |
| 5,776,187 A | 7/1998 | Krueger et al. |
| 5,800,531 A | 9/1998 | Cosgrove et al. |
| 5,810,873 A | 9/1998 | Morales |
| 5,814,096 A | 9/1998 | Lam et al. |
| 5,885,228 A | 3/1999 | Rosenman et al. |
| 5,947,993 A | 9/1999 | Morales |
| 5,951,540 A | 9/1999 | Verbeek |
| 5,972,016 A | 10/1999 | Morales |

(Continued)

FOREIGN PATENT DOCUMENTS

| | | |
|---|---|---|
| DE | 29911694 U1 | 9/1999 |
| DE | 102004019254 B8 | 11/2005 |

(Continued)

OTHER PUBLICATIONS

Extended European Search Report issued in EP 07112385, mailed Apr. 1, 2008, 11 pages.

(Continued)

*Primary Examiner* — Max Hindenburg
*Assistant Examiner* — Renee Danega
(74) *Attorney, Agent, or Firm* — Faegre Baker Daniels LLP (57) ABSTRACT

A device for measuring an internal dimension of a native cardiac valve annulus includes an elongated support member having a proximal portion and a distal portion. A measuring portion is coupled to the distal portion, and an indicator is coupled to the proximal portion of the support member. The measuring portion is biased towards a deployed configuration such that when deployed it applies an outwardly directed radial force to the native valve annulus.

12 Claims, 10 Drawing Sheets

(56) References Cited

U.S. PATENT DOCUMENTS

| | | |
|---|---|---|
| 6,019,739 A | 2/2000 | Rhee et al. |
| 6,024,737 A | 2/2000 | Morales |
| 6,051,002 A | 4/2000 | Morales |
| 6,063,102 A | 5/2000 | Morales |
| 6,110,200 A * | 8/2000 | Hinnenkamp ............... 623/2.11 |
| 6,202,272 B1 | 3/2001 | Jackson |
| 6,277,110 B1 | 8/2001 | Morales |
| 6,309,383 B1 | 10/2001 | Campbell et al. |
| 6,350,281 B1 | 2/2002 | Rhee |
| 6,352,547 B1 | 3/2002 | Brown et al. |
| 6,387,117 B1 | 5/2002 | Arnold et al. |
| 6,402,780 B2 | 6/2002 | Williamson et al. |
| 6,454,799 B1 | 9/2002 | Schreck |
| 6,481,262 B2 | 11/2002 | Ching et al. |
| 6,506,201 B2 | 1/2003 | Di Caprio et al. |
| 6,510,722 B1 | 1/2003 | Ching et al. |
| 6,598,307 B2 | 7/2003 | Love et al. |
| 6,629,350 B2 | 10/2003 | Motsenbocker |
| 6,678,962 B1 | 1/2004 | Love et al. |
| 6,726,713 B2 | 4/2004 | Schaldach et al. |
| 6,730,118 B2 | 5/2004 | Spenser et al. |
| 6,769,161 B2 | 8/2004 | Brown et al. |
| 6,846,324 B2 | 1/2005 | Stobie |
| 6,915,560 B2 | 7/2005 | Austin |
| 6,966,924 B2 | 11/2005 | Holmberg |
| 6,968,607 B2 | 11/2005 | Motsenbocker |
| 6,981,982 B2 | 1/2006 | Armstrong et al. |
| 6,988,881 B2 | 1/2006 | Motsenbocker et al. |
| 7,007,396 B2 | 3/2006 | Rudko et al. |
| 7,021,114 B2 | 4/2006 | Perreault |
| 7,069,794 B2 | 7/2006 | Motsenbocker et al. |
| 7,258,698 B2 | 8/2007 | Lemmon |
| 7,338,484 B2 | 3/2008 | Schoon et al. |
| 7,357,814 B2 | 4/2008 | Gabbay |
| 7,367,984 B2 | 5/2008 | Kulcinski et al. |
| 7,427,291 B2 | 9/2008 | Liddicoat et al. |
| 7,455,690 B2 * | 11/2008 | Cartledge et al. ............. 623/2.37 |
| 2001/0049558 A1 | 12/2001 | Liddicoat et al. |
| 2002/0035390 A1 | 3/2002 | Schaldach et al. |
| 2002/0042651 A1 | 4/2002 | Liddicoat et al. |
| 2002/0129820 A1 | 9/2002 | Ryan et al. |
| 2002/0198594 A1 | 12/2002 | Schreck |
| 2003/0114913 A1 | 6/2003 | Spenser et al. |
| 2003/0125805 A1 | 7/2003 | Johnson et al. |
| 2003/0192164 A1 | 10/2003 | Austin |
| 2004/0039436 A1 | 2/2004 | Spenser et al. |
| 2004/0123437 A1 | 7/2004 | Kokish |
| 2004/0193259 A1 | 9/2004 | Gabbay |
| 2004/0225356 A1 | 11/2004 | Frater |
| 2005/0166389 A1 | 8/2005 | Perreault et al. |
| 2005/0197695 A1 | 9/2005 | Stacchino et al. |
| 2005/0197696 A1 | 9/2005 | Gomez Duran |
| 2005/0229670 A1 | 10/2005 | Perreault |
| 2005/0234537 A1 | 10/2005 | Edin |
| 2005/0240256 A1 | 10/2005 | Austin |
| 2005/0267529 A1 | 12/2005 | Crockett et al. |
| 2005/0283232 A1 | 12/2005 | Gabbay |
| 2006/0004469 A1 | 1/2006 | Sokel |
| 2006/0074486 A1 | 4/2006 | Liddicoat et al. |
| 2006/0178740 A1 | 8/2006 | Stacchino et al. |
| 2006/0265855 A1 | 11/2006 | Stenzel |
| 2007/0027534 A1 | 2/2007 | Bergheim et al. |
| 2007/0056346 A1 | 3/2007 | Spenser et al. |
| 2007/0061009 A1 | 3/2007 | Spenser et al. |
| 2007/0100356 A1 | 5/2007 | Lucatero et al. |
| 2007/0162113 A1 | 7/2007 | Sharkawy et al. |
| 2007/0173861 A1 | 7/2007 | Strommer et al. |
| 2008/0147076 A1 * | 6/2008 | Geisert et al. ............... 606/90 |
| 2008/0262603 A1 | 10/2008 | Giaquinta et al. |
| 2009/0018570 A1 | 1/2009 | Righini et al. |
| 2009/0192603 A1 | 7/2009 | Ryan |
| 2010/0262043 A1 | 10/2010 | Sauter et al. |

FOREIGN PATENT DOCUMENTS

| | | |
|---|---|---|
| EP | 155245 B1 | 5/1990 |
| EP | 401199 B1 | 1/1995 |
| EP | 515324 B1 | 12/1996 |
| EP | 778009 B1 | 7/2002 |
| EP | 1353420 B1 | 3/2005 |
| EP | 1174098 B1 | 3/2006 |
| EP | 1690515 B1 | 7/2008 |
| EP | 1570809 B1 | 1/2009 |
| GB | 2083362 A | 3/1982 |
| JP | 11332997 A | 12/1999 |
| WO | WO9639942 A1 | 12/1996 |
| WO | WO 97/24989 A1 | 7/1997 |
| WO | WO 98/14138 A1 | 4/1998 |
| WO | WO 99/53864 A1 | 10/1999 |
| WO | WO 99/55255 A1 | 11/1999 |
| WO | WO 00/06052 A1 | 2/2000 |
| WO | WO 99/53866 A8 | 2/2000 |
| WO | WO 00/21464 A1 | 4/2000 |
| WO | WO 00/30565 A1 | 6/2000 |
| WO | WO 01/21076 A1 | 3/2001 |
| WO | WO 01/76510 A8 | 1/2002 |
| WO | WO 02/11646 A1 | 2/2002 |
| WO | WO 01/021110 A9 | 8/2002 |
| WO | WO 01/021103 A9 | 10/2002 |
| WO | WO 02/092257 A1 | 11/2002 |
| WO | WO 2005/082578 A1 | 9/2005 |
| WO | WO 2006/088712 A1 | 8/2006 |
| WO | WO 2006/117016 A1 | 11/2006 |
| WO | WO 2006/127089 A1 | 11/2006 |
| WO | WO 2006/136930 A1 | 12/2006 |
| WO | WO 2007/030825 A3 | 6/2007 |
| WO | WO 2006/007401 A3 | 1/2008 |
| WO | WO 2001/021097 A3 | 3/2008 |
| WO | WO2008089365 A2 | 7/2008 |

OTHER PUBLICATIONS

Partial European Search Report issued in EP 07112385, mailed Jan. 4, 2008, 5 pages.
Search Report from European Patent Application 07106697.1, dated Aug. 8, 2007.
Extended European Search Report issued in EP 07106697, mailed Aug. 21, 2007, 6 pages.
EP Communication issued in EP 07112385 on Jul. 30, 2009.
Extended European Search Report issued in EP 10168449, dated Aug. 19, 2010, 3 pages.
International Search Report and Written Opinion issued in PCT/US2010/028873, dated Jun. 15, 2010, 11 pages.

* cited by examiner

UNIVERSAL VALVE ANNULUS SIZING DEVICE

CROSS-REFERENCE TO RELATED APPLICATION

This application claims the benefit of provisional application No. 61/161,462, filed Mar. 19, 2009, entitled "UNIVERSAL VALVE ANNULUS SIZING DEVICE," which is herein incorporated by reference in its entirety.

TECHNICAL FIELD

The present invention relates to devices and methods for measuring the size of an anatomical valve annulus, and more particularly, to devices for use in measuring the size of a cardiac valve annulus in conjunction with implantation of an expandable prosthetic heart valve.

BACKGROUND

Various sutureless heart valve prostheses have been considered for replacing diseased or defective native cardiac valves (e.g., the aortic valve). One such type of prosthetic heart valve includes a radially collapsible/expandable stent, which supports a set of valve leaflets. Typically, the stent is radially contracted during implantation of the prosthetic valve at the desired location. To optimize performance, the stent is sized such that, if unrestrained, it can expand to a diameter somewhat greater than the diameter of the annulus of the valve to be replaced and/or the vessel proximate to the native valve (i.e., in the case of an aortic valve prosthesis, the ascending aorta).

To ensure proper anchoring and operation of the prosthetic valve in situ, it is helpful to assess the size of the patient's anatomical valve annulus. The annulus includes dense, fibrous rings attached to the adjacent atrial or ventricular muscle fibers. In some valve replacement procedures, the physician excises the defective native valve leaflets to prepare the annulus for implantation of the replacement valve. Typically, physicians use a set of sizing obturators, which are provided by various heart valve manufacturers, to obtain an estimate of the diameter of the native valve annulus. These sizing obturators typically include a cylindrical body having a flat, annular flange thereabout. The physician typically advances the flange to a location adjacent the superior aspect of the valve annulus, but does not typically advance the flange to an intra-annular position. This process may require the physician to repeatedly introduce various sizing obturators to the valve annulus to obtain this size estimate. This procedure requires much time and effort and offers minimal accuracy. This procedure also relies significantly on the skill of the implanting physician, as proper sizing is largely based upon the skill and technique of the physician.

SUMMARY

The present invention, according to exemplary embodiments, is a device for measuring an internal dimension of a native cardiac valve annulus. The device includes an elongated support member having a proximal portion and a distal portion including an end having a bore and a longitudinal slot, a measuring band having a first end and a second end, the first end disposed within the bore and the second end coupled to the distal portion, a shaft extending through the support member, the shaft having a distal end coupled to the first end of the measuring band and a proximal end, and an indicator coupled to the proximal end of the shaft, the indicator adapted to provide an indication of the internal dimension. The measuring band has a contracted configuration in which the band is at least partially wound about a transverse axis and an expanded configuration in which the band is substantially unwound.

The present invention, according to other embodiments, is a device for measuring an internal dimension of a native cardiac valve annulus, the device comprising a body portion and a measuring portion, the measuring portion including an expandable element configured to substantially adapt to the shape of the annulus.

The present invention, according to other embodiments, is a method of implanting an expandable prosthetic valve at a native valve annulus. The method includes removing a native valve leaflet, debriding the native valve annulus, stressing the valve annulus by applying a force similar to that applied by a prosthetic valve, obtaining an estimate of the perimeter of the valve annulus, selecting an appropriate prosthetic valve based on the estimate, and implanting the appropriate prosthetic valve at the native valve annulus.

The present invention, according to another embodiment is a method of implanting an expandable prosthetic valve at a native valve annulus. The method includes removing a native valve leaflet, debriding the native valve annulus, stressing the valve annulus by applying a force similar to that applied by a prosthetic valve, obtaining an estimate of the perimeter of the valve annulus, selecting an appropriate prosthetic valve based on the estimate, and implanting the appropriate prosthetic valve at the native valve annulus.

Another embodiment of the present invention is a kit for implanting a sutureless prosthetic heart valve, the kit comprising a sizing tool for measuring an internal dimension of a native cardiac valve annulus, the sizing tool comprising an expandable element configured to substantially adapt to the shape of the annulus, and an expandable, stented prosthetic heart valve. The prosthetic heart valve, in some embodiments, generates a first radial force against the valve annulus upon implantation and the expandable element generates a second radial force, the second radial force differs from the first radial force by less than about 10%.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
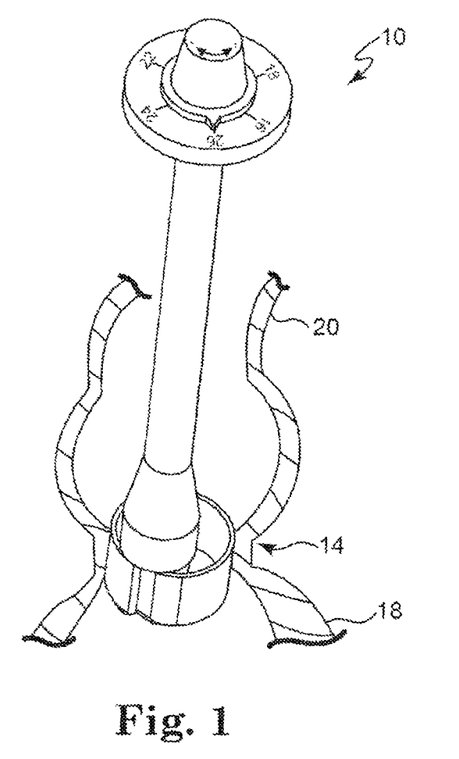
FIG. 1 is a perspective partial cut-away view of a valve sizer in a deployed state according to one embodiment of the present invention.

FIG. 1 is a perspective partial cut-away view of a valve sizing device 10 in a deployed state within a patient's aortic valve annulus 14, according to one embodiment of the present invention. While the following description of the various embodiments of the present invention are generally described with reference to an aortic valve annulus, it is also useful for measuring a dimension of other cardiac valve annuli, including for example the pulmonary valve annulus. Further, the devices of the present invention can be used to measure other valve annuli as well as the inner dimensions of vessels or other tubular anatomical structures.

As is known, and as shown in FIG. 1, the left ventricle 18 is coupled to the ascending aorta 20. During normal operation, the left ventricle 18 pumps blood out of the heart through the aortic valve and into the ascending aorta 20. The aortic valve is a semilunar valve including a set of valve leaflets surrounding the aortic annulus 14, which is defined by the periannular tissue located at the most distal portion of the left ventricular outflow tract. The annulus 14 includes dense, fibrous rings attached to the adjacent atrial or ventricular muscle fibers. As shown in FIG. 1, the sizing device 10 is positioned to allow measurement of a diameter and/or a perimeter of the aortic annulus 14. As shown, access to the annulus 14 is obtained from a superior position through an incision in the ascending aorta 20. In the illustrated embodiments, the native aortic valve leaflets have been removed. It will be appreciated, however, that removal of the native valve leaflets is not a requirement of the sutureless aortic valve replacement procedure. That is, in various embodiments, the valve prosthesis can be implanted without removing the native valve leaflets.

The sizing device 10 may be used in connection with implantation of an expandable/contractible replacement heart valve of the type generally known in the art. The sizing device 10 may be used, for example, in connection with any sutureless aortic valve prostheses, for example, including percutaneously delivered aortic valve prostheses. In various exemplary embodiments, the sizing device 10 is used in connection with implantation of any of the prosthetic valves disclosed in co-pending and commonly assigned U.S. patent application Ser. Nos. 11/066,346 and 11/352,021, the disclosures of which are incorporated herein by reference in their entireties.

Figure 2A:
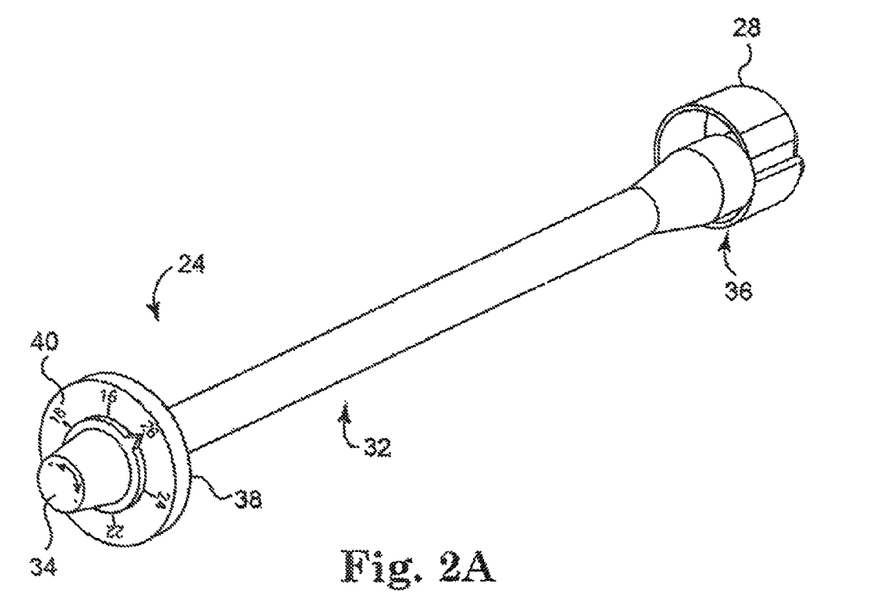
FIGS. 2A-2B are perspective views of the valve sizer of FIG. 1 in deployed and undeployed configurations.
Figure 2B:
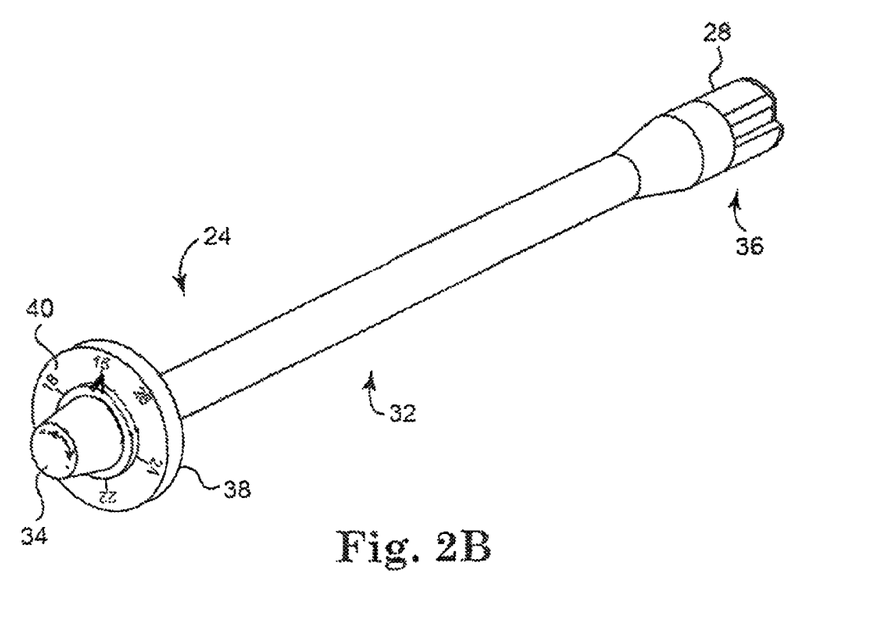

FIGS. 2A-2B are perspective views of the valve sizer of FIG. 1 in deployed and undeployed configurations, respectively. As shown, the sizing device 10 includes a main body portion 24 supporting a measuring portion 28. As shown in FIG. 2A, the measuring portion or band 28 is disposed in an expanded configuration, in which the measuring band 28 has an effective diameter larger than that of the distal end of the main body portion 24, while in FIG. 2B, the measuring band 28 is disposed in a collapsed configuration, in which it has an effective diameter about equal to that of the distal end of the main body portion 24. This expandable/collapsible design facilitates delivery of the tool using standard minimally-invasive delivery techniques and instruments. This design also provides the device 10 with the ability to measure a wide variety of valve annuli, each having a distinct diameter or perimeter dimension.

As further shown in FIGS. 2A-2B, the main body portion 24 includes an elongated support member 32, which couples an adjustable member or knob 34 at its proximal end to an adjustment mechanism 36 at its distal end. In various embodiments, a shaft or coupling rod (not shown) extends through an internal lumen in the elongated support member 32 and rotationally couples the adjustable knob 34 to the adjustment mechanism 36. In various embodiments, the support member 32 includes a linkage or plurality of linkages, which allow adjustment of the orientation and shape of the handle (e.g., both angularly and rotatably) relative to the adjustable portion 36. In various embodiments, the support member 32 may include a locking mechanism to allow the physician to lock the position of the support member when desired. In various embodiments, all or a portion of the support member 32 may be made flexible in addition to or in lieu of the inclusion of the linkages, thereby providing alternative or additional flexibility in orienting the adjustment mechanism 36 inside the valve annulus.

According to some embodiments, the device 10 is configured such that the adjustment mechanism 36 responds to movement imparted on the adjustable knob 34. For example, during use, a physician could apply a rotational force having a desired magnitude to the adjustable knob 34. This force in-turn causes a corresponding rotation of the adjustment mechanism 34. This rotation of the adjustment mechanism causes deployment of the measuring band 28. According to other embodiments, as further explained below, the measuring band 28 is biased to an open or expanded position, such that it self-expands inside the valve annulus, which causes rotation of the adjustment mechanism 36, which in-turn causes rotation of the adjustable knob 34. In some embodiments, the adjustable knob 34 or the adjustment mechanism 36 include a latch or lock for retaining the measuring band in the collapsed configuration. The physician may then manipulate this latch or lack at an appropriate time, to allow the measuring band to deploy or expand.

An annular member 38 is coupled near a proximal end of the elongated support member 32 adjacent the adjustable knob 34. The annular member or indicator 38 includes indicia 40 disposed circumferentially about the annular member. These indicia are configured to indicate a degree of deployment of the measuring band 28. In the embodiment of FIGS. 2A and 2B, for example, the indicia 40 include various numbers representative of the diameter of the measuring band in millimeters. In other embodiments, the indicia 40 are configured to indicate an effective length (i.e., the length extending out of the adjustment mechanism 36) of the measuring band. Of course, one skilled in the art, will recognize that a wide variety of other indicia may be useful in connection with a valve sizing procedure.

Figure 3A:
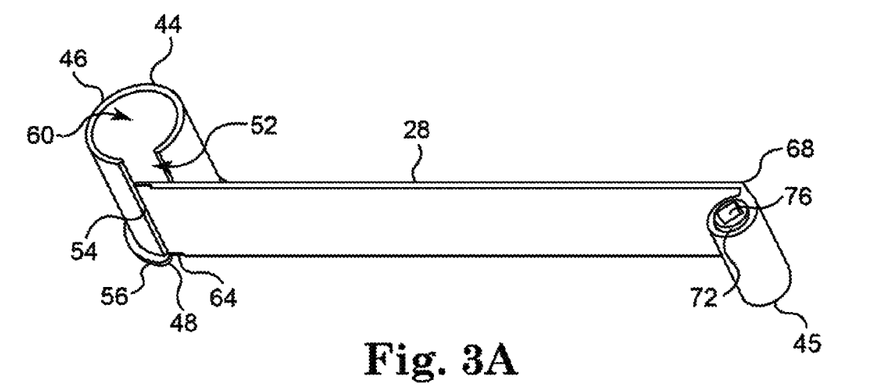
FIGS. 3A-3C are a perspective view, a top plan view and an end plan view, respectively, showing the measuring band in a fully extended configuration.
Figure 3B:
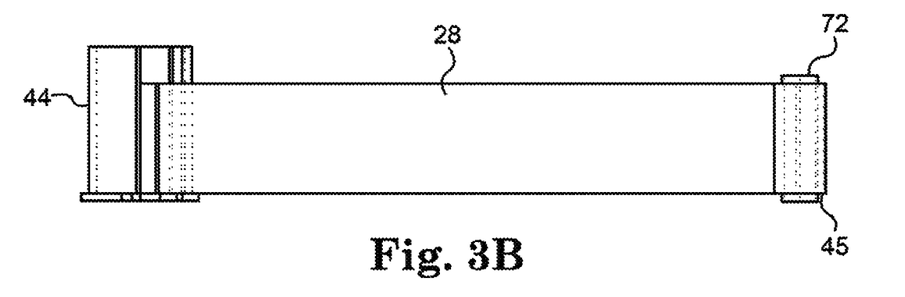
Figure 3C:
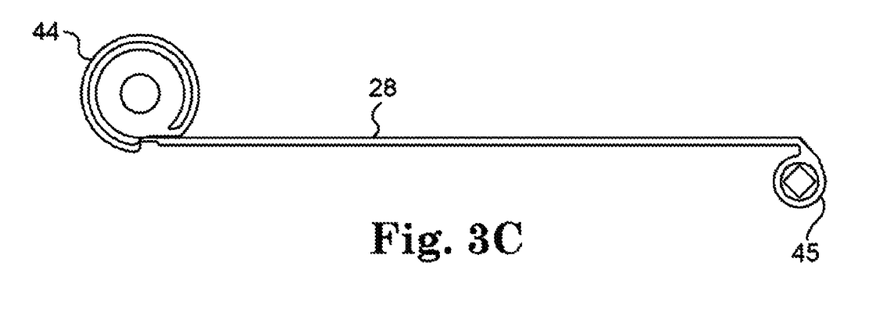

FIGS. 3A-3C show various views of the adjustment mechanism 36 located at a distal end of the sizing device 10. In the configuration shown in FIGS. 3A-3C, for purposes of illustration only, the measuring band 28 has been partially disassembled from the adjustment mechanism 36. These figures to not show a configuration obtained by the measuring band 28 during actual use of the sizing device 10. As shown in FIG. 3A, the adjustment mechanism 36 includes a cylindrical holder 44, the measuring band 28, and a hub portion 45. As shown, the cylindrical holder 44, which has a proximal end 46 and a distal end 48, is structurally separate from the elongated support member 32. In such embodiments, the proximal end 46 of the cylindrical holder 44 is adapted to couple to a distal end of the sizing device 10, such as for example by use of an interference fit with a distal portion of the support member 32. According to other embodiments, the cylindrical holder is an integrally formed portion of the distal end of the elongated support member 32. In either case, the cylindrical holder is fixed both longitudinally and rotationally during use of the device.

The cylindrical holder 44 includes an opening or slot 52 extending longitudinally through a portion thereof. In some embodiments, the slot 52 extends along the entire length of the holder 44 from the proximal end 46 to the distal end 48. Adjacent the slot 52 is a coupling edge 54. As shown, the holder 44 also includes an annular lip 56 located at the distal end 48. In other embodiments, the holder 44 includes an annular lip at the proximal end 46 as well. The cylindrical holder 44 defines an internal, central chamber or bore 60.

As shown in FIGS. 3A-3C, the measuring band 28 includes an elongated portion extending from a proximal end 64 to a distal end 68. The proximal end 64 is coupled to the holder 44 at or near the coupling edge 54. The distal end 68 of the measuring band 28 is coupled to the hub portion 45. As shown, the hub portion 45 includes a protrusion 72 defining an internal engagement portion 76. The protrusion 72 and engagement portion 76 facilitation coupling of the hub portion 45 to the coupling rod, which extends from the adjustment mechanism 36 to the proximal end of the sizing device 10. The measuring band 28 may be made from any material having suitable physical characteristics. In various embodiments, the band 28 is made from a biocompatible polymeric or metallic material. In embodiments where the band 28 is self-expandable, the band is made from a polymer or metal having shape memory and/or superelastic properties. Once such class of superelastic materials well known in the art are nickel-titanium alloys, such as nitinol. According to one exemplary embodiment, the measuring band has a length of between about 150 and 190 mm, a height of between about 1 and 10 mm, and a thickness of about 0.05 and 2 mm. In other embodiments, the measuring band may include other dimensions as appropriate for use of the ban in measuring the circumference of a valve annulus.

In some embodiments, the measuring band 28 includes a longitudinally extending radiopaque portion to facilitate visualization of the measuring band during use of the device. In other embodiments, the longitudinally extending edge (or edges) of the measuring band 28 are tapered or otherwise softened, to help minimize trauma to the valve annulus 14 or adjacent tissue during a sizing procedure.

According to various embodiments the hub portion 45 and the measuring band 28 are removable from the holder 44. In these embodiments, the measuring band 28 and hub portion 45 of the sizing device 10 are readily disposable after use, while the remaining portions of the device may be sterilized and reused by the physician. In these embodiment, for example, the measuring band can be removed by unwinding and expanding the measuring band and then manipulating the measuring band around the distal annular lip 56. The measuring band 28 and hub 45 can then be slid distally out of the holder 44 for disposal. A new, sterile measuring band 28 and hub 45 can then be inserted into the holder 44, and the engagement portion 76 coupled to the coupling rod.

Figure 4A:
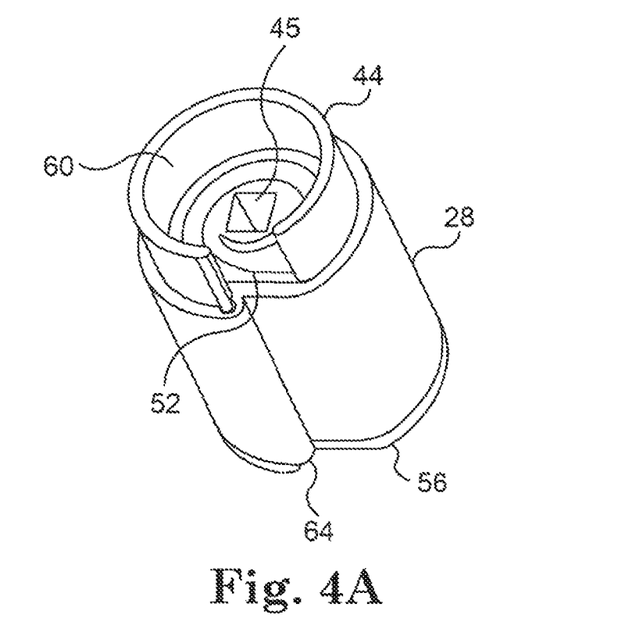
FIGS. 4A-4B are a perspective view and an end plan view of the measuring band in a contracted configuration.
Figure 4B:
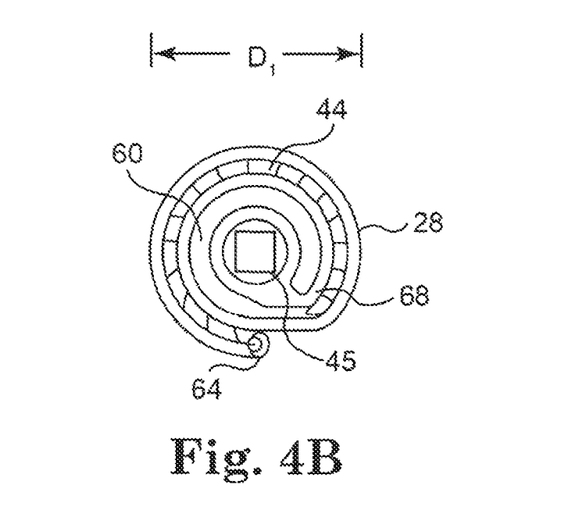

FIGS. 4A-4B show the adjustment mechanism 36 in an assembled, collapsed configuration. For illustration purposes only, the cylindrical holder 44 is shown separated from the elongated support member 32. As shown in FIGS. 4A-4B, the measuring band 28 is wound about the holder 44 in a clockwise direction, such that it extends along an outer surface of the holder 44, extends through the slot 52, and extends along an internal surface of the holder 44 in the central chamber 60. The proximal end 64 of the measuring band 28 is attached at or near the coupling edge of the holder 44, and the distal end 68 of the measuring band is coupled to the hub portion 45. In this configuration, the measuring band has a minimal effective diameter ($D_1$), which facilitates access to the valve annulus 14 using standard minimally invasive access techniques and instruments. In the embodiment shown, the annular lip 56 extends radially outward from the holder a distance about equal to the thickness of the measuring band 28. In this embodiment, the leading (distal) edge of the measuring band is thus covered or protected by the annular lip 56. As shown in FIGS. 4A-4B, in the assembled configuration, the hub portion 45 is located inside the central chamber 60, with portions of the measuring band 28 wound thereabout.

Figure 5A:
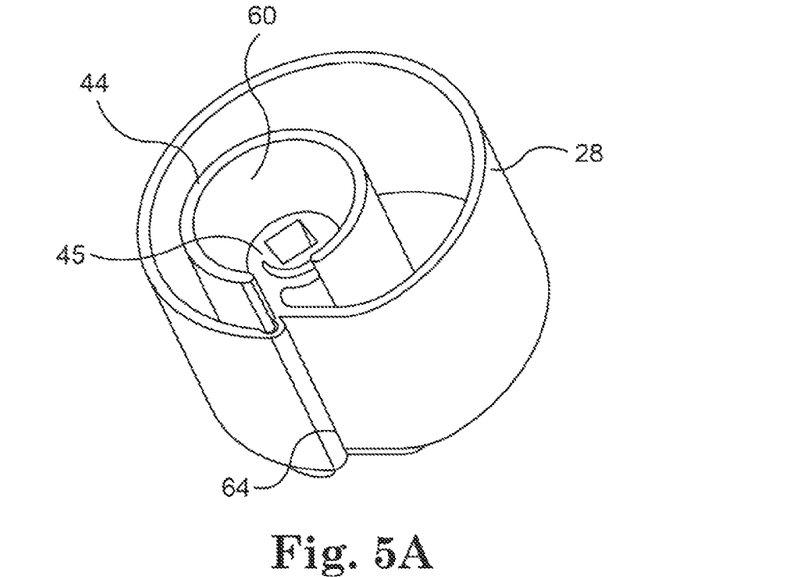
FIGS. 5A-5B are a perspective view and an end plan view of the measuring band in a deployed configuration.
Figure 5B:
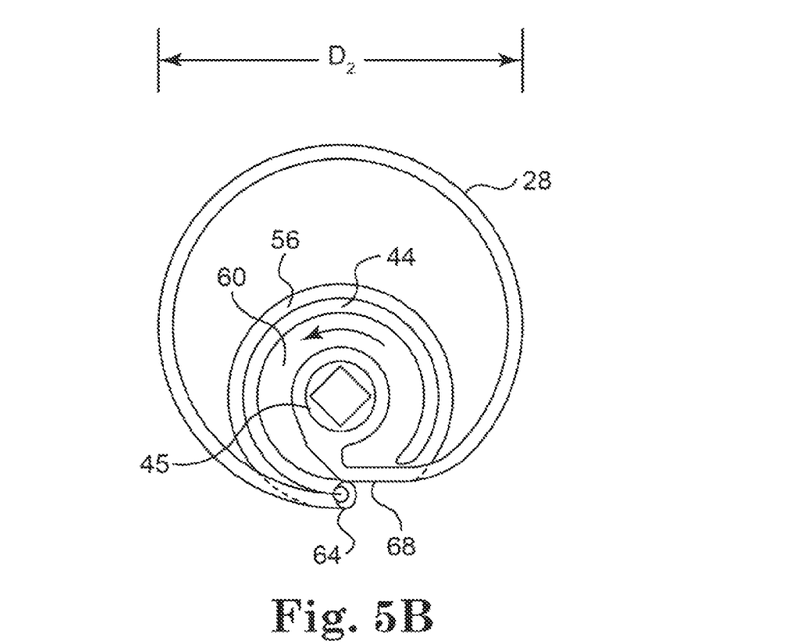

FIGS. 5A-5B show the adjustment mechanism 36 in an assembled, expanded configuration. Again, for illustration purposes, the cylindrical holder 44 is shown separated from the elongated support member 32. As shown, in the expanded configuration, the measuring band 28 is at least partially unwound, which results in an the measuring band 28 defining an expanded effective diameter ($D_2$). As shown, the proximal portion 64 of the measuring band 28 remains attached to the holder 44, and the distal portion 68 remains attached to the hub portion 45. The hub portion 45, however, has rotated in the direction indicated by the arrow in FIG. 5B, to allow the measuring band to extend out through the slot 52 and away from the holder 44. The effective length (i.e., the length extending out from the holder 44) corresponds to an amount of rotation of the central hub 45. As the hub rotates in a counter-clockwise direction, the measuring band expands outwardly from the holder 44, and as the hub rotates in a clockwise direction, the measuring band contracts towards the holder 44. In the most expanded configuration, the hub portion 45 remains inside the holder 44, but all or nearly all portions of the measuring band 28 have extended out through the slot 52.

Figure 6A:
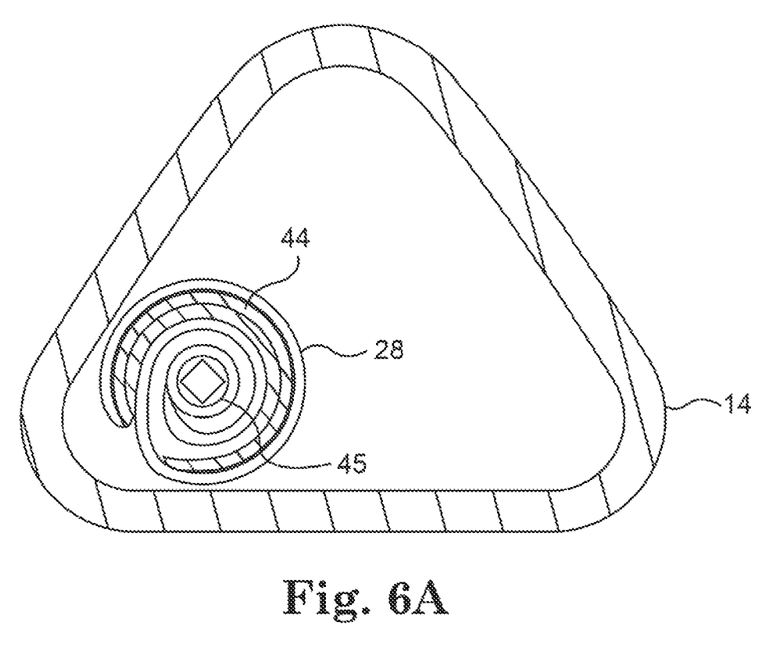
FIGS. 6A-6B are schematic views showing the measuring band in a contracted and a deployed configuration, respectively.
Figure 6B:
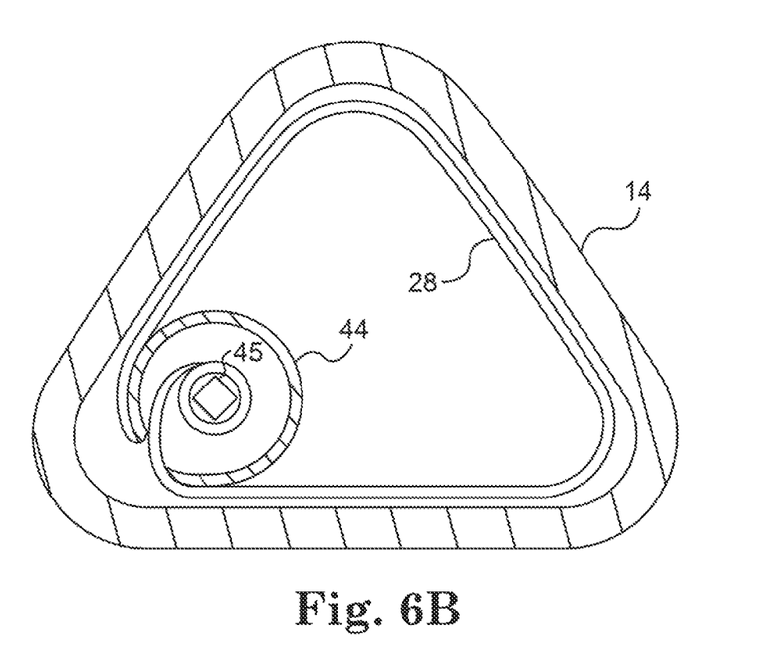

FIGS. 6A-6B show schematic sectional views of a distal end of the sizing device 10, which has been placed at an intra-annular location by the implanting physician. In the illustrated embodiment, the native valve annulus 14 is not precisely cylindrical in cross section, but instead has a slightly trigonal sectional configuration. While the sizing device 10 of the present invention is well suited to measure a diameter or perimeter dimension of a cylindrical annulus, it is also well suited to measure the effective diameter or perimeter of a non-cylindrical valve annulus. Likewise, the device of the present invention is able to measure the perimeter of a valve annulus that includes calcification or other imperfections.

As shown in FIG. 6A, the physician has located the adjustment mechanism 36 of the sizing device 10 inside the valve annulus, with the measuring band 28 in a contracted configuration. Next, the physician activates the adjustment mechanism 36 to enable the measuring band 28 to expand radially outward into contact with an internal surface of the valve annulus, as shown in FIG. 6B. According to various embodiments, the materials and dimensions of the measuring band 28 are selected to enable the band to readily expand outward and to substantially or entirely conform to the inner surface of the valve annulus.

According to some embodiments, the measuring band 28 is unwound and expanded manually by the implanting physician. In these embodiments, the physician can expand and contract the measuring band by turning the adjustable knob 34. As explained above, the adjustable knob 34 is coupled (using, for example, a coupling rod) to the adjustment mechanism 36. Specifically, in various embodiments, the adjustable knob is coupled to the hub portion 45 of the adjustment mechanism. By turning the adjustable knob 34, the physician can effect a corresponding rotation of the hub portion, which in turn will effect an unwinding or unfurling of the measuring band 28. In these embodiments, the physician can rotate the adjustable knob 34 until she feels a certain degree of resistance, which corresponds to an amount of radial force applied by valve annulus 14 against the measuring band 28. When the physician determines that she has caused an appropriate amount of force against the valve annulus, she can read the indicia 40 on the handle, which indicates the corresponding diameter or effective length of the measuring band 28.

In some embodiments, the sizing device 10 includes a torque limiting device of the type known in the art. This torque limiter is placed between the knob 34 and the adjustment mechanism 36 and prevents the physician from applying an excessive force of a magnitude that could cause damage to the native valve annulus.

According to other embodiments, the measuring band 28 is made from a superelastic material, which is biased to the fully expanded configuration. In one such exemplary embodiment, the measuring band is made from a material and has dimensions selected such that the measuring band will expand to a diameter greater than the largest expected valve annulus diameter. In one embodiment, for example, the measuring band 28 is biased to an expanded configuration (such as that shown in FIG. 5A) having an effective diameter of greater than about 26 mm. In these embodiments, the material and dimensions of the measuring band 28 are also selected such that the measuring band generates an outward radial force against the inward-facing surface of the valve annulus 14, which radial force approximates that radial force generated by the self-expandable prosthetic valve to be implanted in the valve annulus 14. In some embodiments, the radial force generates by the measuring band 28 differs from the radial force generated by the prosthetic heart valve by not more than 10 percent. In other embodiments, the radial forces differ by not more than 5 percent. In still other embodiments, the radial forces differ by not more than 2 percent.

As will be apparent to the skilled artisan, by setting the self-expanding radial force of the measuring band 28 approximately equal to the radial force generated by the prosthetic valve to be implanted, the sizing device 10 may obtain a more accurate measure of the internal dimensions of the valve annulus upon implantation of the prosthetic valve. The implantation of a self-expanding prosthetic valve may result in a change in shape and/or size of the valve annulus 14, which changes will be detected by the sizing device 10 of the present invention. In these embodiments, the implanting physician allows the measuring band to expand inside the valve annulus and then reads the corresponding dimensional information from the indicia 40 disposed on the annular member 38.

According to various embodiments, the measuring band 28 is sufficiently flexible to allow it to substantially conform to the internal surface of the valve annulus 14. In some embodiments, for example, the measuring band 28 is able to readily take on a radius of curvature of less than about 2 mm. This flexibility allows the measuring band to substantially conform to valve annuli having irregular shapes.

Figure 7:
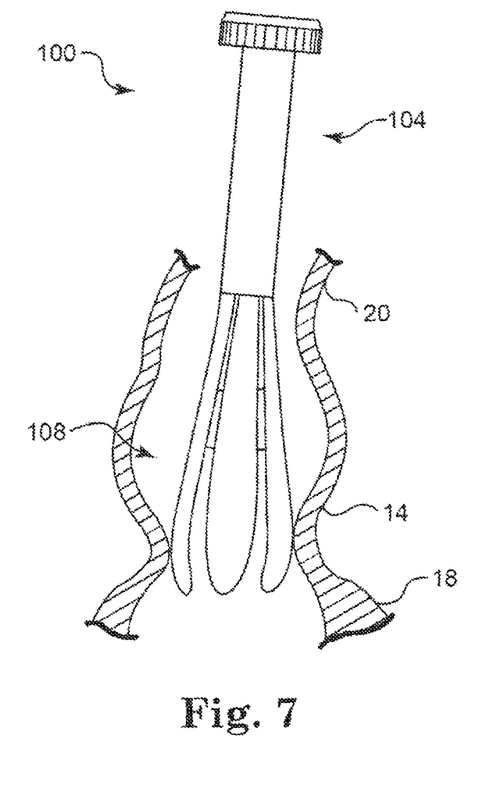
FIG. 7 is a schematic view illustrating a sizing device according to another embodiment of the present invention.

FIG. 7 is a schematic view illustrating a sizing device 100 according to another embodiment of the present invention. As shown in FIG. 7, the device 100 includes a main body portion 104 and a measuring portion 108. The device 100 is shown in one possible operating configuration with the main body portion or handle 104 extending through a vessel downstream from the valve and the measuring portion located generally insider the valve annulus. In FIG. 7, the measuring portion 108 is shown in a deployed or expanded configuration, such that the measuring portion 108 is in contact with an inner wall or surface of the valve annulus.

Figure 8:
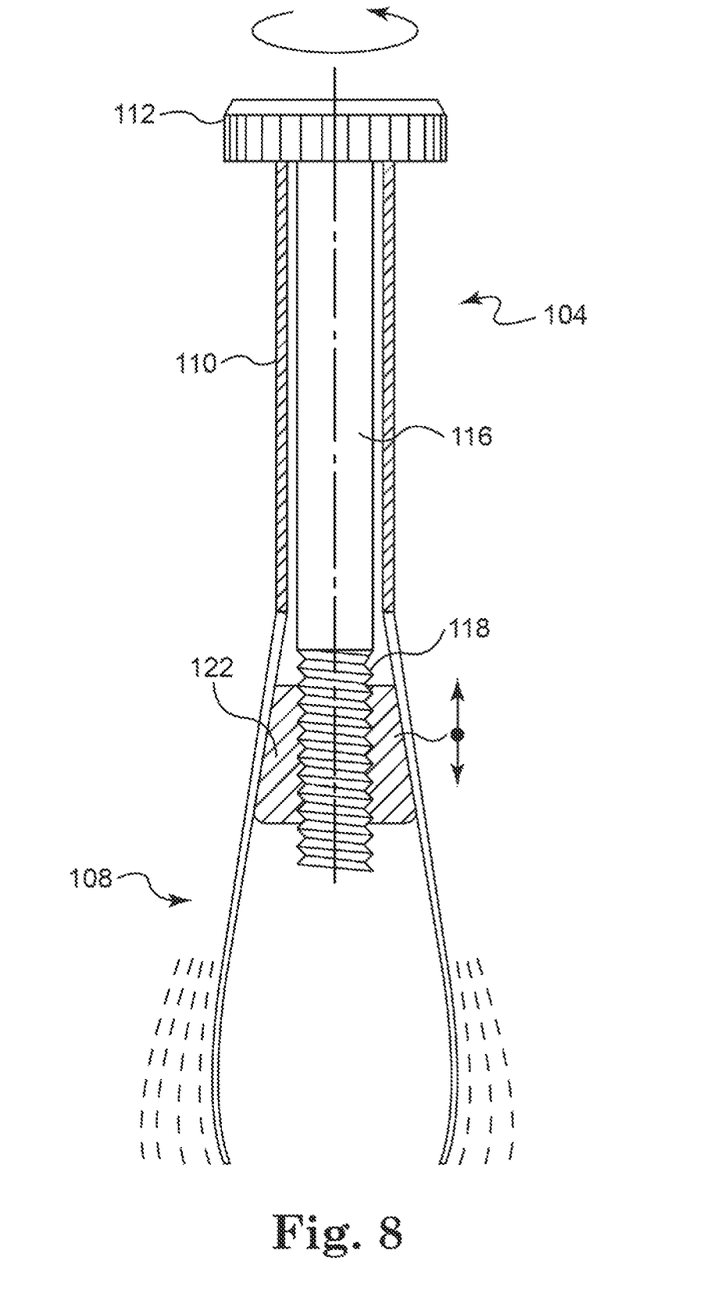
FIG. 8 is a partial sectional view of the sizing device shown in FIG. 7.

FIG. 8 shows a partial sectional view of the sizing device 100. As shown, the main body portion includes an elongated support member 110, which couples an adjustable member 112 to the measuring portion 108. As further shown in FIG. 8, the main body portion houses or contains a torque member or rod 116, which is coupled to the adjustable member 112 at a proximal end and includes a threaded distal end 118. The threads of the rod 116 engage corresponding threads of a tapered element 122, such that a rotation applied to the adjustable member 112 causes rotation of the rod 116, which in turn causes longitudinal motion of the tapered element 122 with respect to the main body portion 104. As the tapered element is moved towards the main body portion 104, it slides along an interior surface of the measuring portion 108, which in turn causes the measuring portion to expand outwardly. Accordingly, a user of the device 100 can apply a torque to the adjustable member 112 to cause expansion or deployment of the measuring portion 108, until the measuring portion contacts the interior surface of the annulus. In some embodiments, the adjustable member includes an associates scale which is configured to indicate the corresponding diameter or circumference of the measuring portion 108.

According to other embodiments, the measuring portion 108 is self-expanding. In some such embodiments, the measuring portion 108 is expanded in an unbiased position, such that it defines an overall diameter that is slightly larger than a diameter of the target valve annulus. In exemplary embodiments, the measuring portion 108 is made from a polymer or metal having shape memory and/or superelastic properties. Once such class of superelastic materials well known in the art are nickel-titanium alloys, such as nitinol. In some embodiments, the measuring portion is held in a collapsed or compressed configuration by a sheath or tube disposed over the elongated support member 110. The measuring portion 108 is then deployed (i.e., allowed to self-expand) by retracting the sheath and allowing the measuring portion to expand radially into contact with an inner surface of a valve annulus. In such embodiments, the elongated support member may include indicia which are disposed axially along the shaft such that the indicia correspond to a diameter or circumference of the measuring portion 108. In this fashion, the indicia will provide the user with an indication of the diameter or circumference of the target valve annulus.

Figure 9:
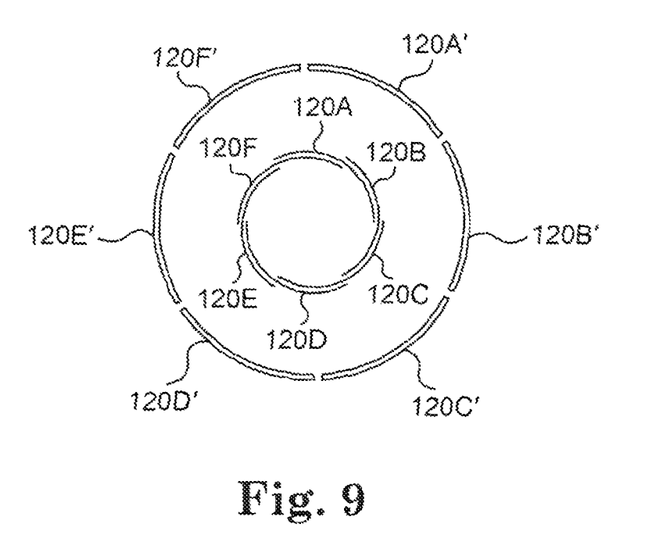
FIG. 9 is a schematic view of an exemplary embodiment of the measuring portion of the sizing device shown in FIG. 7 in deployed and undeployed configurations.

FIG. 9 shows a schematic view of an exemplary embodiment of the measuring portion 108. As shown in FIG. 9, in this embodiment, the measuring portion includes a plurality of measuring elements or petals 120A to 120F. In various exemplary embodiments, the measuring portion 108 may include more or fewer petals 120, as appropriate for measuring the desired valve annulus. As shown in FIG. 9, the petals 120 are expandable (as described above) from a collapsed configuration to and expanded configuration. An exemplary expanded configuration is shown by the elements or petals marked 120A' to 120F'.

Figure 10:
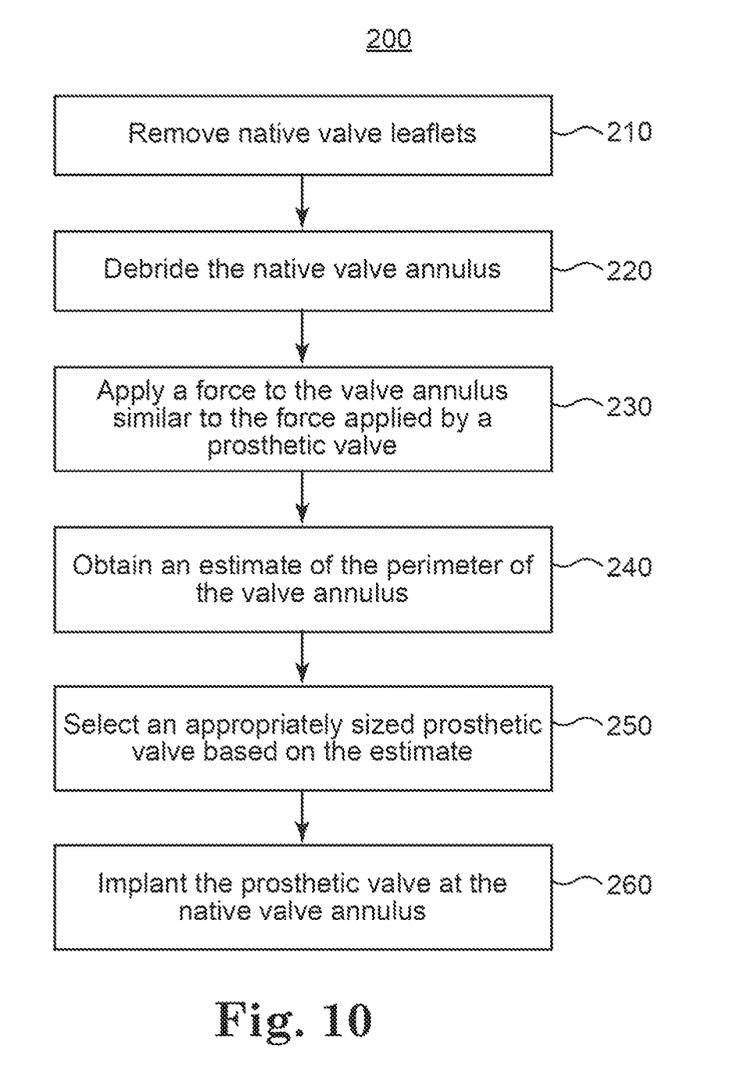
FIG. 10 is a flow chart showing a method of sizing a valve annulus, according to an embodiment of the present invention.

FIG. 10 is a flowchart illustrating one exemplary technique 200 for using the sizing device 10 or 100 of the present invention. As shown in FIG. 7, in some embodiments, the physician first removes the native anatomical valve leaflets from the valve (block 210). The physician then, in some embodiments, debrides or otherwise smoothes out the tissue at the valve annulus (block 220). The physician then introduces the sizing device 10 of the present invention to an intra-annular location and activates or releases the measuring band until it applies an outwardly directed force similar to that applied by the prosthetic valve to be implanted (block 230). While this force is being applied to the valve annulus, the physician reads an estimate of the annulus diameter or perimeter from the device (block 240). Based on this estimate of the annulus dimension, the physician selects an appropriately sized prosthetic valve (block 250). The physician then implants the appropriately sized valve at the native valve annulus (block 260).

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. A device for measuring an internal dimension of a native cardiac valve annulus, the device comprising:
   an elongated support member having a proximal portion and a distal portion, the distal portion including an end defining an inner bore and having a longitudinal slot extending therethrough;
   a measuring band having a first end and a second end, the first end disposed within the bore and the second end coupled to the distal portion of the support member, wherein a portion of the measuring band between the first end and second end extends through the slot;
   a shaft extending through the support member, the shaft having a distal end coupled to the first end of the measuring band and a proximal end; and
   an indicator coupled to the proximal end of the shaft, the indicator adapted to provide an indication of the internal dimension of the measuring band;
   wherein the measuring band has a contracted configuration in which the band is at least partially wound about a transverse axis, so as to have a contracted diameter equal to or less than a bore diameter, and an expanded configuration in which the band is substantially unwound and has an effective diameter larger than that of the end of the distal portion of the support member.

2. The device of claim 1 wherein the measuring band is self-expanding and is adapted to apply an outwardly directed radial force against the valve annulus.

3. The device of claim 2 wherein the measuring band is removable from the distal portion of the support member.

4. The device of claim 1 wherein the measuring band is unwound to apply an outwardly directed radial force to the valve annulus in order to measure the internal dimension of the valve annulus.

5. The device of claim 1 wherein the measuring band is unwound such that the measuring band applies an outwardly directed radial force to the native valve annulus, and the indicator indicates a degree of deployment of the measuring band.

6. A device for measuring an internal dimension of a native cardiac valve annulus, the device comprising an elongated support member having a proximal portion and a distal portion, a measuring band coupled to the distal portion, and an indicator coupled to the proximal portion, and a torque applicator coupled to the proximal portion of the elongated support member, wherein the torque applicator is capable of transmitting a torque provided by the user to a first end of the measuring band, the measuring band is self-expanding and biased towards a deployed configuration such that when deployed the measuring band applies an outwardly directed radial force to the native valve annulus, and the indicator indicates a degree of deployment of the measuring band.

7. The device of claim 6 wherein the torque applicator includes a torque limiter capable of restricting the amount of torque transmitted by the user to the first end of the measuring band to a desired torque level.

8. A device for measuring an internal dimension of a native cardiac valve annulus, the device comprising a body portion and a measuring band, the measuring band configured to self-expand radially outward into contact with an internal surface of the valve annulus and comprises a flexible material configured to allow the measuring band to substantially conform to the shape of the annulus, wherein the measuring band has a contracted configuration in which the measuring band is at least partially wound about a transverse axis and has an effective diameter about equal to that of a distal end of the body portion and an expanded configuration in which the measuring band is substantially unwound and has an effective diameter larger than that of the distal end of the body portion.

9. The device of claim 8 wherein the measuring band is removable from the distal portion of the support member.

10. The device of claim 8 wherein the measuring band is made from a superelastic material.

11. The device of claim 8 wherein the measuring band is selected such that the measuring band generates an outwardly directed radial force against the valve annulus.

12. The device of claim 11 wherein the dimensions of the measuring band are selected such that the outwardly directed radial force has a magnitude about equal to a self-expanding prosthetic valve to be implanted.

* * * * *